United States Patent
Jansen et al.

(10) Patent No.: US 7,297,649 B2
(45) Date of Patent: *Nov. 20, 2007

(54) SILICOBORONCARBONITRIDE CERAMICS AND PRECURSOR COMPOUNDS, METHOD FOR THE PRODUCTION AND USE THEREOF

(75) Inventors: Martin Jansen, Leonberg (DE); Utz Müller, Bonn (DE); Jürgen Clade, Würzburg (DE); Dieter Sporn, Würzburg (DE)

(73) Assignee: Max-Planck-Gesellschaft Zur Forderung der Wissenschaften E.V., Munich (DE)

( * ) Notice: Subject to any disclaimer, the term of this patent is extended or adjusted under 35 U.S.C. 154(b) by 515 days.

This patent is subject to a terminal disclaimer.

(21) Appl. No.: 10/380,605

(22) PCT Filed: Sep. 14, 2001

(86) PCT No.: PCT/EP01/10667

§ 371 (c)(1),
(2), (4) Date: Sep. 16, 2003

(87) PCT Pub. No.: WO02/22624

PCT Pub. Date: Mar. 21, 2002

(65) Prior Publication Data

US 2005/0119106 A1 Jun. 2, 2005
US 2007/0155611 A9 Jul. 5, 2007

(51) Int. Cl.
*C04B 35/563* (2006.01)
*C04B 35/565* (2006.01)
*C04B 35/583* (2006.01)
*C04B 35/584* (2006.01)

(52) U.S. Cl. .................... 501/96.2; 501/93; 501/96.4; 556/402; 562/806; 564/9

(58) Field of Classification Search .............. None
See application file for complete search history.

(56) References Cited

FOREIGN PATENT DOCUMENTS

| DE | 41 07 108 A | 9/1992 |
|----|----|----|
| DE | 198 17 680 A | 10/1999 |
| EP | 0 453 350 A1 | 4/1991 |
| WO | 0 502 399 | 9/1992 |
| WO | WO 98 10118 | 3/1998 |
| WO | WO 98 45302 | 10/1998 |

OTHER PUBLICATIONS

"Preparation of Chlorodisilazanes and some of their Derivatives" authored by Silbiger et al. and published in Inorg. Chem. (1965), 4(9), 1371-72.*
Chemical Abstracts vol. 57, No. 33, 1962.
Noth, Heinrich et al., "Decomposition of the Si-N Bond by Lewis-acidic boron compounds," Z. Naturforsch., vol. 16b, No. 9 1961, pp. 618-620.
Chemical Abstract: 1977:601623, "Contributions to the Chemistry of Boron. LXXXVII. B,Si-functional (silylamino) boranes: a contribution to the SiN-cleavage by boron halides"; Chemische Berichte (1977), 110(8), 2790-801.

* cited by examiner

*Primary Examiner*—Marc S. Zimmer
(74) *Attorney, Agent, or Firm*—Sutherland Asbill & Brennan LLP

(57) ABSTRACT

The present invention relates to novel alkylhalosilylaminoboranes, in particular alkylchlorosilylaminoboranes, which make it possible to adjust the viscosity of polyborosilazane compounds by varying the number of reactive centers, to novel borosilazane compounds, to novel oligoborosilazane or polyborosilazane compounds which have the structural feature $R^1$—Si—NH—B—$R^2$, where $R^1$ or $R^2$ or both is/are a hydrocarbon radical having from 1 to 20 carbon atoms, in particular an alkyl, phenyl or vinyl group, to silicon borocarbonitride ceramic powder, to ceramic material based on SiC, SiN and BN and to processes for producing each of these and to the use of the polyborosilazanes and the ceramic materials.

46 Claims, No Drawings

SILICOBORONCARBONITRIDE CERAMICS AND PRECURSOR COMPOUNDS, METHOD FOR THE PRODUCTION AND USE THEREOF

The present invention relates to novel alkylhalosilylaminoboranes, in particular alkylchlorosilylaminoboranes, which make it possible to adjust the viscosity of polyborosilazane compounds by varying the number of reactive centers, to novel borosilazane compounds, to novel oligoborosilazane or polyborosilazane compounds which comprise the structural feature $R^1$—Si—NH—B—$R^2$, where $R^1$ or $R^2$ or both is/are a hydrocarbon radical having from 1 to 20 carbon atoms, in particular alkyl, phenyl or vinyl groups, to silicon carbonitride ceramic powder, to ceramic material based on SiC, $Si_3N_4$ and BN, and to processes for the preparation of each and to the use of the polyborosilazanes and the ceramic materials, in particular for the production of fibers.

The production of multinary, nonoxidic ceramics via molecular single component precursors has achieved great importance. It makes it possible to obtain nitridic, carbidic and carbonitridic material systems which are not obtainable via conventional solid state reactions. The products have a high purity, homogeneous element distribution and uniform particle size.

Materials comprising silicon (Si), boron (B) and nitrogen (N) and possibly also carbon (C) and at the same time contain no or very little oxygen display particular properties in respect of the thermal stability and the oxidation resistance. They can be used industrially as bulk materials, in composites, for coatings or as ceramic fibers. The boron-containing materials generally display increased crystallization inhibition, while carbon-containing materials additionally have a higher decomposition temperature than do carbon-free ceramics. Owing to the high mechanical strength, the corrosion resistance at high temperatures, the thermal shock resistance and the high-temperature strength of such materials, they can be used, for example, as reinforcing materials for high-temperature composites and are employed in the automobile industry and in the aircraft industry, for example in turbochargers, turbines of jet engines and also for the lining of rocket nozzles and combustion chambers.

The production of ceramics via inorganic polymers is very promising. Crosslinking of molecular structural units gives polymers which can be converted into ceramics by pyrolysis. This route, which has already been followed by Chantrell and Popper, Special Ceramics (editor: E. P. Popper), Academic Press, New York (1964), 87-103, offers new opportunities, in particular for carbidic and nitridic ceramics of main groups 3 and 4.

Winter, Verbeek and Mansmann (Bayer AG) (1975), U.S. Pat. No. 3,892,583, have developed the first spinnable inorganic polymers which have been prepared by aminolysis or ammonolysis of methylchlorosilanes. These were able to be converted into Si/C/N fibers by pyrolysis. The first fibers of commercial significance go back to Yajima who converted polycarbosilanes into carbon-rich SiC fibers (trade name: NICALON), S. Yajima, J. Hayashi, M. Omori (1978), U.S. Pat. No. 4,100,233.

The first homogeneous ceramic in the system Si/B/N/C of the approximate composition $SiBN_3C$ was produced by Wagner, Jansen and Baldus, O. Wagner (1992), EP 502399. The fibers of this material, which is prepared by aminolysis of the single-component precursor trichlorosilylaminodichloroborane (TADB) $Cl_3Si$—(NH)—$BCl_2$, have an excellent property profile, H. P. Baldus, M. Jansen, Dr. Sporn, Science (1999) 285, p. 699. Further improved high-temperature properties are displayed by ceramics from the precursor TSDE (trichlorosilyldichloroborylethane, $Cl_3Si$—[CH—$CH_3$]—$BCl_2$), M. Jansen, H. Jüngermann (Bayer AG) (1997), WO98/45302 A1.

Thus, the high-temperature stability of the ceramics appears to improve with increasing carbon content. This is shown, for example, by the progression of the decomposition temperatures (under inert gas conditions) of the ceramics $Si_3B_3N_7$, $SiBN_3C$ (=$Si_3B_3N_7.C_{2.4}$) and $SiBN_{2.5}C_2$ (=$Si_3B_3N_7.C_6$) which differ essentially only in their carbon content. The thermal stability increases from 1750° C. through 1900° C. up to >2000° C.

The carbon and/or nitrogen content of the ceramics can be varied by the choice of the crosslinking reagents, M. Jansen, H. Jüngermann (1997), U.S. Pat. No. 5,866,705. Thus, TADB can be reacted not only with methylamine or ammonia but also with further amines such as guanidine to form polymers.

In the ceramics mentioned, silicon and boron are coordinated exclusively by nitrogen. The realization of new structural features such as Si—C or B—C bonds in ceramics leads to improved mechanical strength and thermal stability of a ceramic.

The rheological properties, e.g. the viscosity of a polymer for an appropriate processing method, can be adjusted by, for example, thermal pretreatment. However, the known polymers in the system Si/B/N/C have the disadvantage that thermal crosslinking increases continuously in the liquid, i.e. molten, state and the rheological properties such as the viscosity thus do not remain constant during processing. This causes considerable problems such as blocking of the nozzles in the drawing of fibers. Linearly crosslinked molecules are advantageous for achieving a very high elongation in the drawing of fibers. The single-component precursors mentioned have too many reactive centers which lead to multidimensional crosslinking. A polymer consisting predominantly of chains would be advantageous.

It is therefore an object of the invention to provide novel organometallic precursor compounds which can be prepared in high yields and a process for converting these precursor compounds into nitridic ceramics which comprise Si, N, B and C and overcome the abovementioned disadvantages. Adjustment of the number of reactive centers, i.e. the halogen atoms, in the monomeric precursors should make it possible to adjust the rheological properties, in particular to adjust the viscosity, in the reaction to form polyborosilazanes. In particular, the constancy of the rheological properties such as the viscosity in liquid form should be improved thereby. Furthermore, this process should make it possible to prepare ceramics having a high proportion of carbon. In the ceramic, the silicon should be partly coordinated by carbon.

This object is achieved according to the invention by amorphous ceramics or nanocomposites, by their precursor compounds, by the respective processes for producing them and by the use of the polyborosilazanes and the ceramic materials, as disclosed in the claims.

A first aspect of the invention is a compound of the formula (I)

$$R_xHal_{3-x}Si—NH—BR_yHal_{2-y} \qquad (I)$$

where R are each, independently of one another, a hydrocarbon radical having from 1 to 20 carbon atoms, preferably from 1 to 10 carbon atoms, Hal are each, independently of one another, Cl, Br or I,
x=1 or x=2 and
y=0 or y=1.

The compounds of the invention are alkylhalosilylaminoboranes which have at least one hydrocarbon radical bound to the silicon atom. Such compounds have the structural feature C—Si—N—B, C—Si—N—B—C or/and Si—N—B—C and thus have carbon present in the basic skeleton. Such compounds make it possible to produce ceramics which, owing to the increased carbon content and the realization of new structural features such as Si—C or B—C bonds, display improved mechanical strength and thermal stability. The replacement of halogen radicals in the alkylhalosilylaminoboranes of the invention by hydrocarbon radicals, both on the Si and on the B, leads not only to the advantageous introduction of carbon but also to a targeted reduction in the number of reactive halogen atoms. The rheological properties, in particular the viscosity, of the oligomers or polymers formed from the compounds of the invention can be varied or/and set by this means. Particularly advantageous compounds are ones which have three hydrocarbon radicals (x+y=3) containing two halogen atoms capable of crosslinking, which limits multidimensional crosslinking.

In the formula I, the radicals R are each, independently of one another, a hydrocarbon radical having from 1 to 20 carbon atoms, preferably from 1 to 10 carbon atoms. A hydrocarbon radical is a radical which is formed by the elements carbon and hydrogen. According to the invention, the hydrocarbon radical can be branched or unbranched, saturated or unsaturated. The hydrocarbon radical can also contain aromatic groups which may in turn be substituted by hydrocarbon radicals. Examples of preferred hydrocarbon radicals are unbranched saturated hydrocarbon radicals such as $C_1$-$C_{20}$-alkyl, in particular methyl, ethyl, n-propyl, n-butyl, n-pentyl, n-hexyl, n-heptyl, n-octyl, n-nonyl or n-decyl. However, the radicals R can also be branched saturated hydrocarbon radicals, in particular branched $C_3$-$C_{20}$-alkyls such as i-propyl, i-butyl, t-butyl and further branched alkyl radicals. In a further preferred embodiment, the radical R comprises one or more olefinically unsaturated groups. Examples of such radicals are vinyl, allyl, butenyl, pentenyl, hexenyl, heptenyl, octenyl, nonenyl, decenyl, butadienyl, pentadienyl, hexadienyl, heptadienyl, octadienyl, nonadienyl and decadienyl. The radical R can also be an alkyne group, i.e. contain a C≡C bond. In a further preferred embodiment, at least one radical R and preferably all radicals R contains/contain an aromatic group, in particular an aromatic group having from 5 to 10 carbon atoms, in particular 5 or 6 carbon atoms, for instance a phenyl group or an aromatic group, in particular a phenyl group, substituted by a hydrocarbon, in particular a $C_1$-$C_{10}$-hydrocarbon, for instance methylphenyl, dimethylphenyl, trimethylphenyl, ethylphenyl or propylphenyl. Including the substituents, the aromatic radical preferably has from 5 to 20 carbon atoms, in particular up to 10 carbon atoms. The hydrocarbon radicals R can be varied independently of one another.

Particular preference is given to at least one radical R and in particular all radicals R being a $C_1$-$C_{20}$-alkyl group, a phenyl group, a vinyl group or a hydrocarbon radical having from 1 to 3 carbon atoms, in particular methyl, ethyl or propyl and most preferably methyl.

The radical Hal is a halogen atom and is particularly preferably Cl, Br or I, with preference being given to at least one radical Hal and preferably all radicals Hal being Cl. Such compounds are alkylchlorosilylaminochloroboranes.

Particularly preferred embodiments of the invention are compounds of the formula $RHal_2Si$—NH—$BHal_2$, where the radicals R and Hal are as defined above and in particular have the meanings indicated above as preferred. These compounds contain the structural feature C—Si—N—B and have four halogen atoms which are reactive in oligomerization or polymerization. A particularly preferred example of such a compound is (methyldichlorosilylamino)dichloroborane (MADB). Preference is also given to compounds of the formula $R_2HalSi$—NH—$BHal_2$. Such compounds contain two hydrocarbon radicals on the Si atom, as a result of which the carbon content of a ceramic produced from such compounds can be increased further. Furthermore, such compounds have only three halogen atoms which are reactive in oligomerization or polymerization, which makes it possible to achieve further variations in the rheological properties, e.g. the viscosity, of oligomers or polymers formed therefrom. A particularly preferred example of such compounds containing two alkyl radicals and three halogen radicals is (dimethylchlorosilylamino)dichloroborane (DADB). In general, compounds of the formula (I) having the structural element $BHal_2$ are very preferred.

Further preferred compounds include (vinyldichlorosilylamino)dichloroborane, (divinylchlorosilylamino)dichloroborane, phenyldichlorosilylamino)dichloroborane, (diphenylchlorosilylamino)dichloroborane, (ethyldichlorosilylamino)dichloroborane, (diethylchlorosilylamino)dichloroborane and (methylvinylchlorosilylamino)dichloroborane.

In addition, the invention provides compounds having the structural feature —BRHal, so that the boron atom is bound to a hydrocarbon radical and to a halogen. Such compounds preferably have the formula $RHal_2Si$—NH—BRHal or $R_2HalSi$—NH—BRHal. Replacement of a halogen on the boron by a hydrocarbon radical makes it possible to form precursors having a further-increased carbon content and a further-reduced functionality in respect of crosslinking. Thus, compounds $RHal_2Si$—NH—BRHal have only three halogen atoms which are reactive in oligomerization or polymerization and compounds $R_2HalSi$—NH—BRHal have only two such halogen atoms. Preferred examples of compounds of this type are (methyldichlorosilylamino)methylchloroborane, (dimethylchlorosilylamino)methylchloroborane, (phenyldichlorosilylamino)phenylchloroborane, (diphenylchlorosilylamino)phenylchloroborane, (vinyldichlorosilylamino)vinylchloroborane, (divinylchlorosilylamino)vinylchloroborane and (methylvinylchlorosilylamino)phenylchloroborane.

The novel compounds of the formula (I) can be obtained by reacting a compound of the formula (II)

$$R_xHal_{3-x}Si—NH—SiR_3 \qquad (II)$$

with a compound of the formula (III)

$$BR_yHal_{3-y} \qquad (III)$$

at a temperature in the range from −100° C. to +25° C.

Suitable and preferred meanings of R, Hal, x and y are as indicated above. The reaction can be carried out in an organic solvent such as n-hexane or toluene, with, for example, the compound of the formula (II) being added dropwise to a compound of the formula (III) dissolved in an organic solvent. However, preference is given to carrying out the reaction in the absence of a solvent. The reaction temperatures are preferably at least −90° C. and very particularly preferably at least −80° C. and preferably not more than 0° C., particularly preferably not more than −50° C.

Particularly advantageous results are obtained when the reaction is carried out at a temperature of about −78° C.

The novel compounds of the formula (I) can also be obtained by reacting a compound of the formula (II)

$$R_xHal_{3-x}Si-NH-SiR_3 \quad (II),$$

where R are each, independently of one another, a hydrocarbon radical having from 1 to 20 carbon atoms, Hal are each, independently of one another, Cl, Br or I and
x is 1 or 2,
with a compound of the formula (III)

$$BR_yHal_{3-y} \quad (III)$$

where R and Hal are as defined above and
y is 0 or 1, in a molar ratio of from 1:1 to 1:10. The compound of the formula (II) and the compound of the formula (III) are preferably reacted in a molar ratio in the range from 1:1 to 1:5. Particularly advantageous results are obtained in a process in which both the temperature limits indicated here and the molar ratio are adhered to.

The starting compound of the formula (II) $R_xHal_{3-x}Si-NH-SiR_3$ used in the preparation of the novel compound of the formula (I) can be prepared by reacting $R_xSiHal_{4-x}$ and $R_3Si-NH-SiR_3$. In a preferred embodiment, a compound of the formula (IIa) $R_2HalSi-NH-SiR_3$ as starting compound is prepared by reacting $R_2SiHal_2$ and $R_3Si-NH-SiR_3$ in a molar ratio of from 1:1 to 1.5:1, preferably from 1.1:1 to 1.4:1 and particularly preferably from 1.2:1 to 1.3:1. Particularly good results are obtained when the two compounds $R_2SiHal_2$ and $R_3Si-NH-SiR_3$ are used in a molar ratio of about 5:4.

The starting compound of the formula (IIa) $R_2HalSi-NH-SiR_3$ and in particular the silane in which R=$CH_3$ can also be prepared by reacting $R_2SiHal_2$ and $R_3Si-NH-SiR_3$ at a reaction temperature of from 40 to 80° C., in particular up to 60° C. Particularly high yields of the starting compound of >70%, preferably >80%, can be obtained when the reaction is carried out both in the reaction temperature range indicated and in the molar ratio range indicated.

The preparation of the starting compounds and the compounds of the formula (I) will be described in detail once again below using the preparation of the two particularly preferred compounds MADB and DADB as examples.

Surprisingly, the reaction of (1,1-dichlorotetramethyl)disilazane or (chloropentamethyl)disilazane with boron trichloride made it possible to prepare the two new compounds (methyldichlorosilylamino)dichloroborane (MADB) and (dimethylchlorosilylamino)dichloroborane (DADB). These compounds both contain the structural feature C—Si—N—B. MADB has four halogen atoms which are reactive in oligomerization or polymerization, while DADB has only three. The choice of one of the molecules or mixing of the two molecules in any desired ratio thus enables the rheological properties, in particular the viscosity, of the oligomers or polymers to be prepared to be varied. Both molecules are subject matter of the invention.

The starting material (1,1-dichlorotetramethyl)disilazane can be prepared in a yield of over 80% from hexamethyldisilazane and methyltrichlorosilane by stirring at room temperature. The starting material (chloropentamethyl)disilazane can be prepared by reaction of hexamethyldisilazane and dimethyldichlorosilane.

According to the invention, the preparation of (chloropentamethyl)disilazane gives a yield of over 70% when the ratio of the reactants $Me_2SiCl_2$ and hexamethyldisilazane is 5:4 and the reaction temperature is from 40 to 60° C.

According to the invention, the compounds MADB and DADB are formed in yields of 80% and 70% of theory by dropwise addition of the starting materials to boron trichloride, which may be dissolved in an organic solvent (e.g. n-hexane, toluene). The molar ratios of boron trichloride to the starting materials are in the range from 5:1 to 1:1. The reaction temperatures can vary from −100° C. to room temperature, and the preferred value is −78° C.

Monomeric, oligomeric or polymeric borosilazane compounds can be prepared from the novel compounds of the formula (I) by reaction with primary or secondary amines. In such borosilazane compounds, all or some of the halogen atoms of the compound of the formula (I) are replaced by amino groups. Accordingly, the invention further provides borosilazane compounds of the formula (IV):

$$(R'R''N)_qR_xHal_{3-x-q}Si-NH-BR_yHal_{2-y-z}(NR'R'')_z, \quad (IV)$$

where R' and R'' are each, independently of one another, hydrogen or a hydrocarbon radical having from 1 to 20 carbon atoms,
R are each, independently of one another, a hydrocarbon radical having from 1 to 20 carbon atoms,
Hal are each, independently of one another, Cl, Br or I,
q=0, 1 or 2,
x=1 or 2,
y=0 or 1 and
z=0, 1 or 2, with the proviso that $q+z \geq 1$, $x+q \leq 3$ and $z \leq 2$.

The novel borosilazane compounds of the formula (IV) contain at least one hydrocarbon radical which is bound to the Si atom, so that they have the structural feature C—Si—N—B. Compounds in which some of the halogen atoms are replaced by the amino groups R'R''N thus contain hydrocarbon radicals, halogen and amine radicals as substituents on the Si or B. However, preference is given to borosilazane compounds of the formula (IV) in which all of the halogen atoms are replaced by amino groups. Such compounds have the formula (IVa) $(R'R''N)_qR_xSi-NH-BR_y(NR'R'')_z$, where q+x=3 and y+z=2.

If one or more halogen atoms is/are present in the borosilazane compound, it is preferred that Hal is Cl on at least one occurrence and preferably on each occurrence.

Preference is also given to borosilazane compounds of the formula (R'R''N)R Hal Si—NH—B Hal$_2$, (R'R''N)R$_2$ Si—NH—B Hal$_2$, (R'R''N)$_2$ R Si—NH—B Hal$_2$, R$_2$ Hal Si—NH—B Hal(NR'R''), R$_2$ Hal Si—NH—B R(NR'R''), R$_2$ Hal Si—NH—B(NR'R'')$_2$, (R'R''N)R$_2$ Si—NH—B Hal(NR'R''), (R'R''N)R Hal Si—NH—B Hal(NR'R''), (R'R''N)R Hal Si—NH—B R(NR'R''), (R'R''N)R Hal Si—NH—B(NR'R'')$_2$, (R'R''N)$_2$ R Si—NH—B Hal(NR'R''), (R'R"N)R Hal Si—NH—B R Hal, (R'R"N)R$_2$ Si—NH—B R Hal or (R'R"N)$_2$ R Si—NH—B R Hal.

Particular preference is also given to borosilazane compounds in which all halogen atoms have been replaced by amino groups, so that they bear only hydrocarbon radicals or amino groups. Such compounds have the formulae (R'R"N)R$_2$ Si—NH—B(NR'R")$_2$, (R'R"N)R$_2$ Si—NH—B R(NR'R"), (R'R"N)$_2$ R Si—NH—B R(NR'R") or (R'R"N)$_2$ R Si—NH—B(NR'R")$_2$.

In the abovementioned formulae, the radical R has, on each occurrence, the meanings indicated above for the compound (I) and in particular the meanings which are indicated there as preferred. R is particularly preferably a hydrocarbon radical having from 1 to 3 carbon atoms, in particular a methyl, ethyl or propyl radical, or a phenyl radical or a vinyl radical.

The radicals R' and R" are each, independently of one another, hydrogen or a hydrocarbon radical having from 1 to 20 carbon atoms, preferably from 1 to 10 carbon atoms. Preference is given to compounds in which at least one of the radicals R' and R" is a hydrocarbon radical having from 1 to 20 carbon atoms. R' and R" are particularly preferably selected from among $C_1$-$C_{20}$-alkyl groups, in particular $C_1$-$C_3$-alkyl groups such as methyl, ethyl and propyl, and phenyl and vinyl groups.

Particular preference is given to compounds in which both R and R' and R" are methyl on each occurrence. The borosilazane compounds of the invention can be prepared by reacting a compound of the formula (I) with at least, depending on the molecule, from four to eight times the molar amount (number of halogen atoms multiplied by two), preferably at least ten times the molar amount, of a compound of the formula (V) R'R"NH at a temperature of from −80° C. to +300° C. This makes it possible to prepare monomeric or oligomeric or polymeric compounds of the preferred formulae (NR'R")$_2$ R Si—NH—B(NR'R")$_2$ (NR'R")R$_2$ Si—NH—B(NR'R")$_2$ or

[—(NR'R")R Si—NH—B(NR'R")—]$_a$, where a indicates the degree of polymerization, from the compounds of the formula (I), which can be used either individually or in any mixing ratios, by reaction with primary or/and secondary amines. Other monomeric borosilazanes and polyborosilazanes are also possible, in particular those which have transversely crosslinked structures. Use of the compounds MADB and TADB described above by way of example makes it possible to obtain, in particular, compounds of the formula (NRR')$_2$(CH$_3$)Si—NH—B(NRR')$_2$ or (NRR')(CH$_3$)$_2$Si—NH—B(NRR')$_2$ or [(NRR')(CH$_3$)Si—NH—B(NRR')]$_a$. In the monomeric or oligomeric units, the first coordination sphere of each silicon atom consists of carbon and nitrogen atoms. The novel borosilazane compounds of the formula (IV) are preferably prepared by reacting a compound of the formula (I) with at least, depending on the molecule, four to eight times the molar amount (number of halogen atoms multiplied by two), preferably at least ten times the molar amount, more preferably at least twenty times the molar amount, of a compound of the formula (V)

R'R"NH          (V)

at a temperature of from −80° C. to +300° C.

The monomeric or oligomeric units can be converted into polymers by thermal treatment and/or by crosslinking using ammonia or an amine.

The thermal treatment is preferably carried out at temperatures of from −80° C. to +500° C., more preferably up to +300° C. and most preferably up to +200° C. The treatment is preferably carried out under atmospheric pressure or under reduced pressure. However, in some cases it can also advantageously be carried out under superatmospheric pressure.

The invention therefore further provides an oligoborosilazane or polyborosilazane compound which is obtainable by reaction of a compound of the formula (I) or/and a compound of the formula (IV) with a compound of the formula (V) or by polymerization of a compound of the formula (I) or the formula (IV). Such oligoborosilazane or polyborosilazane compounds have the structural feature C—Si—N—B or/and Si—N—B—C. The first coordination sphere of the silicon atoms of the oligoborosilazane or polyborosilazane compounds of the invention preferably consists of both carbon and nitrogen, with the silicon atoms and/or the boron atoms bearing a radical R and the nitrogen atoms bearing a radical R' or R".

In particular, the oligoborosilazane or polyborosilazane compounds have the structural features C—Si—N—B—N—B—N—Si—C, C—Si—N—B—N—Si—N—B or/and Si—N—B—N—Si—N—B—C. The structural features are, in the interests of clarity, represented as linear sequences in which Si is of course always bound to four adjacent atoms, B and N is always bound to three adjacent atoms and C is in each case bound to three or four adjacent atoms. The corresponding bonds have been left out for reasons of clarity but can readily be visualized by a person skilled in the art. Branches can occur at any atom.

B and Si are preferably surrounded by only N or/and C. Particular preference is given to at least one C being bound to each B or/and Si or at least more than 50%, in particular more than 80%, of all B and/or Si. N and C can be surrounded by any atoms, with N—N bonds preferably not being present.

The rheological properties, in particular the viscosity, of the oligoborosilazane or polyborosilazane compounds of the invention can be varied by the choice of the radicals R in the compound of the formula (I) used, by the choice of the radicals R' and R" of the amines used and/or by the type of thermal treatment.

According to the invention, the rheological properties, in particular the viscosity, can be varied for the same thermal treatment and use of the same amines by, for example, the choice of the monomer MADB or DADB or a mixture of these molecules. The methyl group(s) of these single-component precursors can also be entirely or partly replaced by, for example, alkyl, phenyl or vinyl groups so as to give a higher carbon content of the polymers.

The reaction of the monomers with the amines mentioned can be carried out both in open systems and in closed systems. The reaction temperatures are in the range from −78° C. to +500° C., and the reaction time is from 5 minutes to 20 days. The pressure is preferably from 0.001 kPa to $5 \times 10^5$ Pa, more preferably in the range from 0.001 kPa to atmospheric pressure.

Amines suitable for the reaction include, for example, methylamine, ethylamine, dimethylamine, aniline and ammonia. The reaction can be carried out either in the pure components or in an aprotic solvent such as hexane, toluene, THF or methylene chloride. The reaction temperature is preferably at least −78° C., more preferably at least −50° C. and most preferably at least −30° C., and is preferably up to not more than 100° C., more preferably up to not more than 5° C.

The consistency of the polyborosilazanes of the invention thus extends, depending on the radicals R, R' and R" and on the degree of polymerization, from slightly viscous via resinous or waxlike to a solid amorphous or crystalline state. Thermal crosslinking occurs by elimination of an amine radical and formation of new Si—N or B—N bonds. Crosslinking by means of ammonia occurs by replacement of an NR'R" group by an $NH_2$ group which then crosslinks further.

The degree of crosslinking of the polyborosilazanes can thus be set in a targeted manner via the type of polymerization, for example polycondensation by means of thermal treatment or crosslinking using ammonia or an amine. It has been found that, in particular, the processing properties of the polyborosilazanes of the invention to produce fibers can be improved further by setting appropriate reaction parameters in the polycondensation. The process of the invention for preparing an oligoborosilazane or polyborosilazane compound therefore preferably encompasses at least one process step in which a polycondensation is carried out at temperatures of ≦200° C. or/and under reduced pressure, preferably from 0.01 kPa to 10 kPa. Under these reaction conditions, largely "linearized" oligomers or prepolymers having rheological properties which are particularly favorable for the melt spinning process are formed. The curability of the green fibers by means of reactive gases is not impaired. In addition, the homogeneity of the polymer in respect of the element distribution is improved further under these preferred reaction conditions.

Polyborosilazanes which are to be processed further to produce fibers can be obtained from chlorinated precursors such as TADB by reacting the precursors in an inert solvent such as hexane with an amine such as methylamine. This gives, apart from insoluble methylammonium chloride which can be filtered off, a soluble borosilazane oligomer mixture. After distilling off the solvent, the still liquid material can then be polycondensed thermally with elimination of methylamine to give a product which is solid at room temperature and is suitable for the melt spinning process. In the case of the borosilazane oligomer mixture prepared from TADB, temperatures of about 250° C. are advantageously used for the thermal polycondensation. In the case of borosilazane oligomer mixtures prepared from MADB or DADB, higher temperatures of up to 500° C. are often advantageous because of the smaller number of crosslinking sites per monomer unit.

Moreover, compounds having the structural unit ≡Si—N(R)—B≡ are thermally sensitive and can easily decompose to form monosilane and borazine derivatives. Such a decomposition reaction with elimination of monosilanes and oligosilanes can also take place during the polycondensation of borosilazane oligomer mixtures at elevated temperatures. This decomposition reaction often results in the occurrence of inhomogeneities in the element distribution. The advantage of a single-component precursor, namely, in particular, a homogeneous element distribution in the ceramic end product, can be lost by separation into a two-component system which can impair the high-temperature properties of the material. For this reason, process temperatures for the polycondensation of an oligomeric mixture of ≦200° C., preferably ≦180° C., more preferably ≦150° C., and at least 50° C., more preferably ≧100° C., have been found to be advantageous. If this temperature is, in the case of the starting materials selected, not sufficient to give a product which is solid at room temperature, as is required, in particular, for future use in the melt spinning process, the reaction is advantageously carried out under reduced pressure. The pressure is then preferably ≦90 kPa, more preferably ≦10 kPa, particularly preferably ≦1 kPa and even more preferably ≦0.1 kPa.

Under these preferred process conditions, a polyborosilazane having a very homogeneous element distribution is obtained. Furthermore, it has good processability to produce green fibers and can be cured chemically and ceramicized. A further advantage of carrying out the process under reduced pressure is that any monosilazanes or oligosilazanes formed can be distilled off under reduced pressure and thus do not contaminate the product.

The desired silicon borocarbonitride ceramics can be produced from the polyborosilazanes of the invention. Accordingly, the invention further provides a process for producing a silicon carboboronitride ceramic which is characterized in that a monomeric, oligomeric or polymeric borosilazane compound as described herein is heated in an inert or amine-containing and, if carbon-free ceramics are desired, ammonia-containing atmosphere at temperatures of from 800° C. to 2000° C., preferably from 1000° C. to 1800° C. and most preferably from 1350° C. to 1750° C. Aminolysis or ammonolysis reactions and subsequent pyrolysis convert the borosilazanes into a silicon carboboronitride ceramic powder. C—Si—N—B structural units are preferably present in the ceramic and the elements Si, N, B and C are preferably present in an amount of more than 93% by mass, more preferably more than 97% by mass. The silicon carboboronitride ceramic of the invention has, in particular, a low oxygen content of preferably <7% by mass, more preferably <1% by mass and most preferably <0.5% by mass. The process of the invention for producing a silicon carboboronitride ceramic makes it possible to produce ceramics which are virtually free of oxygen. For the reaction of the borosilazane compounds with ammonia, it is possible to utilize all aminolysis or ammonolysis processes known from the literature for tetrachlorosilane, for example reaction with solid or liquid ammonia at low temperatures (U.S. Pat. No. 4,196,178), reaction with gaseous ammonia in an organic solvent (U.S. Pat. No. 3,959,446) or reaction with ammonia in a high-temperature reaction with elimination of hydrogen chloride (U.S. Pat. No. 4,145,224).

The inert atmosphere can be selected from among a noble gas atmosphere, for example an argon or helium atmosphere, a nitrogen atmosphere and an atmosphere comprising another inert gas which does not react with the reactants under the reaction conditions of from 800° C. to 2000° C.

The ceramic yields in the pyrolysis are generally in the range from 65% to 80%. The pyrolysis product is a ceramic material which comprises more than 93% by mass, preferably more than 97% by mass, of the elements Si, N, B and C and contains the structural units C—Si—N—B, Si—N—B—C or/and Si—N—B. The ceramic material preferably contains the structural unit C—Si—N—B—C and in particular the structural units C—Si—N—B—N—B—N—Si—C, C—Si—N—B—N—Si—N—B or/and Si—N—B—

N—Si—N—B—C. The structural features indicated are linear sequences in which Si is of course always bound to four adjacent atoms, B and N are always bound to three adjacent atoms and C is in each case bound to three or four adjacent atoms. The corresponding bonds have been left out in the interests of clarity but can readily be visualized by a person skilled in the art. Branches can occur on any atom.

B and Si are preferably surrounded by only N or/and C. Particular preference is given to at least one C being bound to each B or/and Si or at least to more than 50%, in particular more than 80%, of all B or/and Si. N and C can be surrounded by any atoms, with N—N bonds preferably not being present.

In the pyrolysis, the silicon borocarbonitride ceramic of the invention can be obtained in amorphous or at least partially crystalline form. It is preferably an amorphous silicon borocarbonitride. The silicon borocarbonitride ceramic of the invention has, in particular, a high thermal stability and is inert toward oxygen. The elements present are distributed virtually completely homogeneously within the ceramic. Crystallization of the amorphous material to form a composite ceramic comprising SiC, $Si_3N_3$ and BN can be achieved by aging at a temperature of >1700° C. In such a crystalline composite ceramic, SiC, $Si_3N_3$ and BN crystallites, preferably on a nanometer scale, are distributed essentially fully homogeneously, i.e. are molecularly dispersed. The ceramics of the invention display, in particular, a high thermal stability. Apart from the amorphous ceramics, crystalline ceramics and processes for producing them, the present invention also provides for the use of the monomeric, oligomeric or polymeric borosilazane compounds and the amorphous and at least partly crystalline ceramic materials for producing ceramic fibers, ceramic coatings, shaped ceramic bodies, ceramic sheets or/and ceramic microstructures.

The polyborosilazanes can be processed directly or as solutions in organic solvents to produce shaped bodies, fibers, sheets or coatings. The Theological properties and in particular the viscosity of the polymers can, according to the invention, be matched to requirements by the choice of the compounds of the formula (I) used, e.g. the ratio of MADB and DADB, and also by appropriate choice of the parameters for crosslinking.

The shaped polyborosiloxanes can be subjected to pyrolysis and/or physical or chemical pretreatment, e.g. curing or crosslinking, to make the polymer infusible.

An appropriate treatment for preparing infusible polyborosilanes is described, for example, in DE 195 30 390 A1, where infusible compounds are obtained by reaction with borane-amine adducts. As further reagents for making shaped polyborosilazane bodies, preferably green polyborosilazane fibers, infusible, it is possible to use, in particular, reactive gases such as ammonia, gaseous ethylenediamine, trichlorosilane or dichlorosilane and also boranes (e.g. $B_2H_6$). Hydrogen compounds such as $HSiCl_3$, $H_2SiCl_2$ or $B_2H_6$ are particularly suitable for making polymers containing unsaturated side groups such as vinyl or allyl infusible by means of hydroboration or hydrosilylation reactions.

Microstructures can be produced, for example, by injection molding or lithographic processes. The ceramics are particularly preferably produced in the form of fibers from which, for example, woven or braided fabrics are manufactured. These fabrics can be used as fillers for increasing the strength or toughness of other ceramics.

Furthermore, the borosilazane compounds of the invention can also be used in chemical vapor deposition (CVD) or physical vapor deposition (PVD). Coating of substrates by means of CVD or PVD makes it possible to produce ceramic coatings. Vapor deposition can be carried out as described in the prior art (cf., for example, DE 196 35 848 C1).

The invention is illustrated below by means of some examples, without this implying any restriction:

EXAMPLE 1

Synthesis of (1,1-dichlorotetramethyl)disilazane

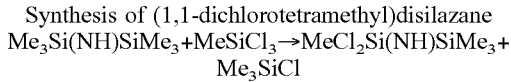

In a 250 ml three-neck flask provided with an overpressure valve and a magnetic stirrer, 178.8 g (1.20 mol, 141.2 ml) of $MeSiCl_3$ together with 64.4 g of hexamethyldisilazane (0.40 mol, 50.0 ml) are stirred at room temperature for two days.

The excess methyldichlorosilane and the trimethylchlorosilane formed are slowly distilled off at room temperature under a continuously decreasing pressure. Purification is carried out by fractional distillation via a Vigreux column.

The boiling point is 39° C. at p=13 mbar, and the yield is 85% of theory.

Mass spectroscopy on (1,1-dichlorotetramethyl)disilazane: m/e=201 ($M^+$), 186 ($M^+$–$CH_3$), 171 ($M^+$–2 $CH_3$), 151 ($M^+$–Cl—$CH_3$). NMR spectroscopy on (1,1-dichlorotetramethyl)disilazane: $^1$H NMR ($C_6D_6$): $\delta$=0.03 ppm (s, 9 H); 0.47 ppm (s, 3 H).

EXAMPLE 2

Synthesis of (chloropentamethyl)disilazane

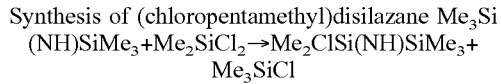

In a 250 ml three-neck flask provided with an overpressure valve and a magnetic stirrer, 51.6 g of $Me_2SiCl_2$ (0.50 mol, 50.0 ml) together with 64.4 g (0.40 mol, 66.8 ml) of hexamethyldisilazane are stirred at 50° C. for two days. The excess methylchlorosilane and the trimethylchlorosilane formed are slowly distilled off at room temperature under a continuously decreasing pressure (diaphragm pump). Purification is carried out by distillation via a Vigreux column. The boiling point is 34° C. at p=10 mbar, and the yield is 70% of theory.

MS (EI): m/e=181 ($M^+$), 166 ($M^+$–$CH_3$), 151 ($M^+$–2 $CH_3$), 146 ($m^+$–Cl). $^1$H-NMR ($C_6D_6$): $\delta$=0.07 (s, 9H); 0.29 (s, 6H).

EXAMPLE 3

Synthesis of 1,1-dichloro-1-vinyltrimethyldisilazane

In a 250 ml three-neck flask, 50 ml of hexamethyldisilazane (38.7 g, 0.24 mol) are admixed with 70 ml of vinyltrichlorosilane (88.9 g, 0.55 mol) and stirred overnight at room temperature. The mixture is fractionated under reduced pressure. After trimethylchlorosilane and excess vinyltrichlorosilane have been distilled off, (1,1-dichloro-1-vinyl)trimethyldisilazane goes over as a clear, colorless liquid. The boiling point is 40° C. at 11 mbar, and the yield is 80%.

$^1$H-NMR spectrum: $\delta$=0.18 ppm: Si(C$\underline{H}_3$); $\delta$=1.40 ppm (broad): N$\underline{H}$; $\delta$=6.17 ppm (multiplet): vinyl. $^{13}$C-NMR spectrum: $\delta$=1.8 ppm: Si($\underline{C}H_3$)$_3$; $\delta$=134.0 ppm: $\underline{C}H$=$CH_2$; $\delta$=137.3 ppm: $\underline{C}H$=$CH_2$.

The vinyl carbon signals have been assigned on the basis of a DEPT spectrum.

IR spectrum [cm$^{-1}$]: 3380 vs, 3198 w, 3145 w, 3070 m, 3022 w, 2960 vs, 2900 m, 1598 s, 1402 vs, 1251 vs, 1180 vs, 1000 vs, 960 vs, 850 vs, 770 vs, 725 vs, 690 vs, 605 sh, 575 vs.

MS: m/e=198 (2 Cl): M$^+$-CH$_3$; m/e=170 (2 Cl): M$^+$-CH$_3$-C$_2$H$_4$; m/e=162: M$^+$-CH$_3$-HCl. The molecular peak is not visible since very rapid elimination of a methyl group evidently takes place. The number of Cl atoms in the fragments was determined by means of the isotope pattern.

EXAMPLE 4

Synthesis of (methyldichlorosilylamino)dichloroborane (MADB)

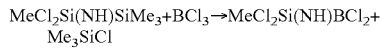

MeCl$_2$Si(NH)SiMe$_3$+BCl$_3$→MeCl$_2$Si(NH)BCl$_2$+Me$_3$SiCl 23.4 g (0.02 mol, 16.36 ml) of BCl$_3$ are placed in a 250 ml three-neck flask provided with a dropping funnel, an overpressure valve and a magnetic stirrer at −78° C. 21.2 g (0.10 mol) of methylchlorodisilazane are added dropwise over a period of 1 hour while stirring. The mixture is allowed to warm up while stirring overnight.

Excess BCl$_3$ and the trimethylchlorosilane formed are slowly distilled off at room temperature under a continuously decreasing pressure (diaphragm pump). The product is a colorless oil. The crude product is purified by distillation. The boiling point is 38° C. at p=13 mbar, and the yield is about 80% of theory.

MS (EI): m/e=194 (M$^+$-CH$_3$), 173 (M$^+$-HCl), 158 (M$^+$-HCl-CH$_3$), 137 (M$^+$-2 HCl). $^1$H-NMR (C$_6$D$_6$): 0.47 (monomer), 0.49 (dimer).

EXAMPLE 5

Synthesis of (dimethylchlorosilylamino)dichloroborane (DADB)

Me$_2$ClSi(NH)SiMe$_3$+BCl$_3$ →Me$_2$ClSi(NH)BCl$_2$+Me$_3$SiCl 29.8 ml (0.36 mol) of BCl$_3$ are placed in a 250 ml three-neck flask provided with a dropping funnel, an overpressure valve and a magnetic stirrer at −78° C. 32.9 g (0.18 mol) of methylchlorodisilazane are added dropwise over a period of 1 hour while stirring. The mixture is allowed to warm up overnight while stirring. Excess BCl$_3$ and the trimethylchlorosilane formed are slowly distilled off at room temperature under a continuously decreasing pressure (diaphragm pump). The product is a colorless oil. The crude product is purified by distillation. The boiling point is 28° C. at p=0.1 mbar, and the yield is about 70% of theory.

MS (EI): m/e=174 (M$^+$-CH$_3$), 154 (M$^+$-Cl), 139 (M$^+$-Cl-CH$_3$). $^1$H-NMR (C$_6$D$_6$): 0.16 (monomer), 0.32 (dimer).

EXAMPLE 6

Synthesis of (vinyldichlorosilylamino)dichloroborane

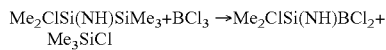

80 ml of BCl$_3$ (114.4 g, 0.98 mol) are placed in a 500 ml three-neck flask at −78° C. While stirring vigorously, a total of 80 ml (81.6 g, 0.38 mol) of vinyldichlorosilylaminotrimethylsilane are added dropwise over a period of 1.5 hours. The mixture is allowed to warm to room temperature overnight and is subsequently fractionated under reduced pressure by means of a 20 cm Vigreux column. After trimethylchlorosilane and excess BCl$_3$ have been separated off, VADB is obtained as main fraction. The boiling point is 33° C. at 12 mbar, and the yield is 65%.

The pure compound polymerizes within a few hours at room temperature to give a white, infusible mass. It is therefore diluted with an inert solvent (e.g. pentane) and stored at low temperature (−20° C.).

$^1$H-NMR spectrum: δ=4.9 ppm (broad): NH; δ=6.3 ppm (multiplet): vinyl. $^{13}$C-NMR spectrum: δ=130.7 ppm: CH=CH$_2$; δ=139.8 ppm: CH=CH$_2$.

The vinyl carbon signals were assigned on the basis of a DEPT spectrum.

IR spectrum [cm$^{-1}$]: 3450 w, 3360 sst, 3075 w, 3040 vw, 2995 vw, 2970 w, 1600 s, 1447 s, 1370 vs, br, 1225 s, 1118 w, 1010 s, 998 s, 990 s, 949 vs, 920 vs, 849 s, 724 vs, 622 vs, 600 vs, 551 vs.

EXAMPLE 7

Synthesis of (dimethylchlorosilylamino)phenylchloroborane

In a 250 ml three-neck flask, a solution of 20 g of phenyldichloroborane (24.5 g, 154 mmol) in 100 ml of absolute pentane is cooled to −78° C. 20 ml of chloropentanemethyldisilazane (18.4 g, 102 mmol) are subsequently added dropwise. The mixture is slowly brought to room temperature and stirred at room temperature for 12 hours. The solvent, the trimethylchlorosilane formed as by-product and excess phenyldichloroborane are subsequently taken off under reduced pressure. This leaves (dimethylchlorosilylamino)phenylchloroborane as a clear, yellowish liquid. Yield: 78%. The substance can also be distilled undecomposed under reduced pressure; an increase in temperature to ≧50° C. leads to decomposition into dimethyldichlorosilane and B-triphenylborazine. The compound is significantly more stable toward air than are the previously known aliphatically or olefinically substituted borosilazanes.

$^1$H-NMR spectrum: δ=0.69 ppm: CH$_3$; δ=4.77 ppm (broad); NH; δ=7.3-7.8 ppm (AA'BB'C spin system): phenyl. $^{13}$C-NMR spectrum: δ=4.7 ppm: CH$_3$; δ=128.5, 132.3, 133.9 and 135.0 ppm: phenyl. IR spectrum [cm$^{-1}$]: 3370 s, 3078 m, 3052 m, 3018 m, 2965 m, 2905 w, 1600 s, 1500 s, 1440 vs, 1405 sh, 1380 vs, 1295 s, 1260 vs, 1230 s, 1180 s, 1150 sh, 1100 vw, 1074 m, 1043 m, 1005 w, 945 sh, 900 vs, 851 vs, 826 vs, 801 vs, 753 s, 700 vs, 680 sh, 635 s, 550 nm.

EXAMPLE 8

Ammonolysis of MADB 80 ml of ammonia which has been dried over sodium are placed in a 500 ml three-neck flask provided with a dropping funnel, an overpressure valve and a magnetic stirrer at −78° C. 15.6 g of MADB dissolved in 100 ml of pentane are added dropwise over a period of 2 hours while stirring. A white precipitate is formed at the point at which the drops enter the ammonia, but this is quickly redissolved in the large excess of ammonia. The reaction mixture is allowed to warm to room temperature overnight while stirring. Colorless hydrochlorides precipitate during this time. The polymer formed is insoluble in organic solvents. The ammonium chloride obtained as by-product is extracted with liquid ammonia. After the extraction, the polymer remains as a colorless powder.

IR (KBr): 3435: ν(N—H), 2964: ν$_{as}$ (C—H), 2903: ν$_s$ (C—H), 1406: ν (B—N), 1265: δ$_s$ (CH$_3$), 994: ν (Si—N), 779: ν (Si—C).

EXAMPLE 9

Ammonolysis of DADB 80 ml of ammonia which has been dried over sodium are placed in a 500 ml three-neck flask provided with a dropping funnel, an overpressure valve and a magnetic stirrer at −78° C. 12.6 g of DADB dissolved in 100 ml of pentane are added dropwise over a period of 2 hours while stirring. A white precipitate is formed at the point at which the drops enter the ammonia, but this is quickly redissolved in the large excess of ammonia. The reaction mixture is allowed to warm to room temperature overnight while. stirring. Colorless hydrochlorides precipitate during this time. The pentane-soluble polymer is separated off from the precipitated ammonium chloride by filtration. The precipitate is washed three times with 20 ml each time of pentane. The pentane is distilled off from the filtrate at room temperature under reduced pressure (10 mbar). This leaves a highly viscous colorless liquid.

IR (KBr): 3451: ν(N—H), 2960: ν$_{as}$ (C—H), 2900: ν$_s$ (C—H), 1382: ν(B—N), 1254: δ$_s$ (CH$_3$), 939: ν (Si—N), 783: (Si—C).

EXAMPLE 10

Aminolysis of MADB 130 ml of methylamine which has been dried over molecular sieves (4 Å) are placed in a 500 ml three-neck flask provided with a dropping funnel, an overpressure valve and a magnetic stirrer at −78° C. 16.9 g of MADB dissolved in 120 ml of pentane are added dropwise over a period of 2 hours while stirring. A white precipitate is formed at the point at which the drops enter the methylamine, but this is quickly redissolved in the large excess of methylamine. The reaction mixture is allowed to warm to room temperature overnight while stirring. Colorless hydrochlorides precipitate during this time. The pentane-soluble polymer is separated off from the precipitated methylammonium chloride by filtration. The precipitate is washed three times with 20 ml each time of pentane. The pentane is distilled off from the filtrate at room temperature under reduced pressure (10 mbar). This leaves a highly viscous colorless liquid.

IR (KBr): 3475: ν(N—H), 2955: ν$_{as}$ (C—H), 2890: ν$_s$ (C—H), 1381: ν (B—N), 929: ν (Si—N), 755: (Si—C).

EXAMPLE 11

Aminolysis of DADB 130 ml of methylamine which has been dried over molecular sieves (4 Å) are placed in a 500 ml three-neck flask provided with a dropping funnel, an overpressure valve and a magnetic stirrer at −78° C. 16.1 g of MADB dissolved in 120 ml of pentane are added dropwise over a period of 2 hours while stirring. A white precipitate is formed at the point at which the drops enter methylamine, but this is quickly redissolved in the large excess of methylamine. The reaction mixture is allowed to warm to room temperature overnight while stirring. Colorless hydrochlorides precipitate during this time. The pentane-soluble polymer is separated off from the precipitated methylammonium chloride by filtration. The precipitate is washed three times with 20 ml each time of pentane. The pentane is distilled off from the filtrate at room temperature under reduced pressure (10 mbar). This leaves a highly viscous colorless liquid.

IR (KBr): 3455: ν(N—H), 2961: ν$_{as}$ (C—H), 2918: ν$_s$ (C—H), 1383: ν (B—N), 1261: δ$_s$ (CH$_3$), 825: ν (Si—N), 778: ν (Si—C).

EXAMPLE 12

Pyrolysis of a Polymer from Examples 5 to 8 to Form an Amorphous Ceramic Powder

The polymer is placed in a boron nitride boat. It is firstly heated at 150 K/h to 700° C. in a stream of argon, maintained at 700° C. for 2 hours and cooled to room temperature at 150 K/h. It is then heated at 300 K/h to 1500° C. in a stream of nitrogen, maintained at 1400° C. for 2 hours and cooled to room temperature at 150 K/h.

The resulting ceramic consists of coarse- to fine-pored black fragments. The X-ray powder diffraction patterns of the four novel networks demonstrate that all samples are X-ray-amorphous after pyrolysis.

Elemental analysis from Example 7 (percent by mass) Si: 26.3, B: 8.9, N: 36.3, C: 18.7, O: 3.9.

EXAMPLE 13

Preparation of a Borosilazane Oligomer Mixture 500 ml of absolute pentane are cooled to −78° C. and 200 ml of methylamine are subsequently condensed into the cooled solvent. While stirring vigorously, 50 ml of MADB or DADB diluted with 100 ml of absolute pentane are then added dropwise over a period of one hour. After removal of the cold bath, two phases are observed; the upper phase comprises the oligomer mixture dissolved in pentane while the lower phase comprises methylammonium chloride dissolved in liquid methylamine. The mixture is warmed to room temperature overnight, resulting in evaporation of the excess methylamine. The methylammonium chloride which has now crystallized is filtered off under protective gas and washed with 3×50 ml of absolute pentane. The solvent is taken off from the combined filtrates under reduced pressure. This gives an oligomer mixture which is a viscous liquid at room temperature.

EXAMPLE 14

Preparation of a Polyborosilazane

An oligomer mixture obtained by aminolysis of MADB or DADB as described in Example 10 is heated at 50°/h to 200° C. under a protective gas atmosphere. After a hold time of 3 hours, the material is allowed to cool to room temperature and the reaction flask is connected to a distillation apparatus. The contents of the flask are then heated at 50°/h to 150° C. under reduced pressure and this temperature is maintained until no more by-products go over. The temperature is then increased to 200° C. over the course of 1 hour. After a hold time of 3 hours, the contents of the flask are again allowed to cool to room temperature, giving a solid, brittle, colorless, clear product.

EXAMPLE 15

Rheological Characterization of a Polyborosilazane Prepared from MADB

On a rotation rheometer, the viscosity is firstly determined in a temperature range from 120 to 145° C. An Arrhenius plot gives a viscosity of 100 Pa·s at 131° C. Oscillation tests are carried out at this temperature. The region of linear viscoelasticity is firstly determined by variation of the deformation amplitude γ from 0.01 to 10 (this range of linear viscoelasticity extends to γ=1) and the variation of the storage modulus G' and the loss modulus G" on varying the oscillation frequency from 6 to 600 Hz at γ=0.1 is then determined. During the test, G' rises from 9.6 Pa to 2480 Pa; G" rises from 724 Pa to 60600 Pa. This gives a loss factor (tan δ) of 61.2 at ω=10 Hz. According to R. Beyreuther and R. Vogel, Intern. Polymer Processing XI, Hanser Publishers, Munich 1996, a loss factor of at least 10 is necessary for a readily spinnable polymer.

EXAMPLE 16

Rheological Characterization of a Polyborosilazane Prepared from DADB

On a rotation rheometer, the viscosity is firstly determined in a temperature range from 70 to 100° C. An Arrhenius plot gives a viscosity of 100 Pa·s at 88.6° C. Oscillation tests are carried out at this temperature. The region of linear viscoelasticity is firstly determined by variation of the deformation amplitude γ from 0.01 to 10 (this range of linear viscoelasticity extends to γ=0.7) and the variation of the storage modulus G' and the loss modulus G" on varying the oscillation frequency from 0.1 to 100 Hz at γ=0.1 is then determined. During the test, G' rises from 55 Pa to 54000 Pa; G" rises from 0.3 Pa to 150 Pa. This gives a loss factor (tan δ) of 200 at ω=1 Hz.

EXAMPLE 17

Production of Green SiBNC Fibers from a polyborosilazane Prepared and Characterized as Described in the above Examples The polyborosilazane is placed in a heatable pressure vessel, melted at 90° C. and extruded through a capillary nozzle (Ø 300 μm) under a pressure of pure nitrogen (p=4-8 bar). The polymer thread leaving the nozzle is wound up on a godet (takeoff velocity=300 m/min) and plaited.

EXAMPLE 18

Curing of Green Fibers Produced as Described in Example 13 by a Batch Method using Ammonia or Amines The green fibers are introduced into a batch reactor in which an atmosphere of pure $NH_3$ or ethylenediamine-containing $N_2$ (EDA content in the range from 0.5 to 1.5%) is provided. After aging for 24 hours at room temperature, the temperature of the reactor is increased to 60° C. and aging is continued for a further 24 hours. The cured green fibers can subsequently be pyrolyzed at 1200° C. without defects (fused regions, conglutination) occurring. The ceramic fibers typically have a tensile strength of from 1 to 1.5 GPa, a modulus of elasticity of from 100 to 150 GPa and an oxygen content of ≦1% by weight.

EXAMPLE 19

In-Situ Shaft Curing of Green Fibers During the Spinning Process

The polyborosilazane is spun as described in Example 13 to give green fibers. However, a mixture of $N_2$ with about 1-2% of trichlorosilane is passed into the spinning shaft during the process. It has to be ensured by means of an extraction device that no trichlorosilane reaches the spinning nozzle. The spun and cured green fibers can subsequently be pyrolyzed at 1200° C. The ceramic fibers typically have a tensile strength of from 1 to 1.5 GPa, a modulus of elasticity of from 100 to 150 GPa and an oxygen content of ≦1% by weight.

The invention claimed is:

1. A compound of the formula (I)

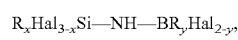

where R are each, independently of one another, a hydrocarbon radical having from 1 to 20 carbon atoms,
Hal are each, independently of one another, Cl, Br or I,
x=1 or 2 and
y=0 or 1.

2. A compound as claimed in claim 1, characterized in that Hal is Cl on each occurrence.

3. A compound as claimed in claim 1, characterized in that R is, independently on each occurrence, a hydrocarbon radical having from 1 to 3 carbon atoms, a $C_1$-$C_{20}$-alkyl group, a phenyl group or a vinyl group.

4. A process for preparing a compound as claimed in any of claims 1 to 3, comprising reacting a compound of the formula (II)

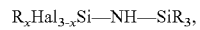

where R are each, independently of one another, a hydrocarbon radical having from 1 to 20 carbon atoms,
Hal are each, independently of one another, Cl, Br or I and
x=1 or 2,
with a compound of the formula (III)

where R and hal are as defined above and
y=0 or 1,
at a temperature in the range from −100° C. to +25° C.

5. A process for preparing a compound as claimed in any of claims 1 to 3, comprising reacting a compound of the formula (II)

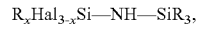

where R are each, independently of one another, a hydrocarbon radical having from 1 to 20 carbon atoms,
Hal are each, independently of one another, Cl, Br or I and
x=1 or 2,
with a compound of the formula (III)

where R and Hal are as defined above and
y=0 or 1,
in a molar ratio of from 1:1 to 1:10.

6. The process as claimed in claim 4, characterized in that Hal is Cl on each occurrence.

7. The process as claimed in claim 4, characterized in that R is, independently on each occurrence, a hydrocarbon radical having from 1 to 3 carbon atoms, a $C_1$-$C_{20}$-alkyl group, a phenyl group or a vinyl group.

8. The process as claimed in claim 5, characterized in that Hal is Cl on each occurrence.

9. The process as claimed in claim 5, characterized in that R is, independently on each occurrence, a hydrocarbon radical having from 1 to 3 carbon atoms, a $C_1$-$C_{20}$-alkyl group, a phenyl group or a vinyl group.

10. The process as claimed in claim 6, characterized in that R is, independently on each occurrence, a hydrocarbon radical having from 1 to 3 carbon atoms, a $C_1$-$C_{20}$-alkyl group, a phenyl group or a vinyl group.

11. The process as claimed in claim 8, characterized in that R is, independently on each occurrence, a hydrocarbon radical having from 1 to 3 carbon atoms, a $C_1$-$C_{20}$-alkyt group, a phenyl group or a vinyl group.

12. A borosilazane compound of the formula (IV)

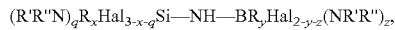

$$(R'R''N)_q R_x Hal_{3-x-q} Si\text{---}NH\text{---}BR_y Hal_{2-y-z}(NR'R'')_z,$$

where R' and R" are each, independently of one another, hydrogen or a hydrocarbon radical having from 1 to 20 carbon atoms, R are each, independently of one another, a hydrocarbon radical having from 1 to 20 carbon atoms, Hal are each, independently of one another, Cl, Br or I, q=0, 1 or 2, x=1 or 2, y=0 or 1 and z=0, 1 or 2, with the proviso that $q+z \geq 1$, $x+q \leq 3$ and $y+z \leq 2$.

13. A borosilazane compound as claimed in claim 12, characterized in that Hal is Cl on each occurrence.

14. A borosilazane compound as claimed in claim 12, characterized in that R is, on each occurrence, a hydrocarbon radical having from 1 to 3 carbon atoms, a $C_1$-$C_{20}$-alkyl group, a phenyl group or a vinyl group.

15. A borosilazane compound as claimed in claim 12, characterized in that R', R" are each selected independently from among $C_1$-$C_3$-alkyl, $C_1$-$C_3$-alkenyl, in particular vinyl, and phenyl.

16. A borosilazane compound as claimed in claim 13, characterized in that R is, on each occurrence, a hydrocarbon radical having from 1 to 3 carbon atoms, a $C_1$-$C_{20}$-alkyl group, a phenyl group or a vinyl group.

17. A borosilazane compound as claimed in claim 13, characterized in that R', R" are each selected independently from among $C_1$-$C_3$-alkyl, $C_1$-$C_3$-alkenyl, in particular vinyl, and phenyl.

18. A borosilazane compound as claimed in claim 14, characterized in that R', R" are each selected independently from among $C_1$-$C_3$-alkyl, $C_1$-$C_3$-alkenyl, in particular vinyl, and phenyl.

19. A process for preparing a borosilazane compound as claimed in any of claims 12-15 or 16-18, comprising reacting a compound of the formula (I) as defined in any of claims 1 to 3 with at least 4 to 8 times the molar amount of a compound of the formula (V) R'R"NH at a temperature of from −80° C. to +300° C., where R' and R" are as defined in claim 12, 15, 17 or 18.

20. An oligohorosilazane or polyborosilazane compound obtainable obtained by reaction of a compound of the formula (I) as defined in any of claims 1 to 3 or a compound of formula (IV) as defined in any of claims 12-15 or 16-18 with a compound of the formula (V) R'R"NH, where R' and R" are as defined in claim 12-15, 17 or 18, or by polymerization of a compound of the formula (I) or the formula (IV), characterized in that it has the structural features C—Si—N—B, Si—N—B—C er/and-or C—Si—N—B—C.

21. A process for preparing an oligoborosilazane or polyborosilazane compound, comprising polymerizing or reacting one or more compounds of the formula (I) as defined in any of claims 1 to 3 or/and one or more compounds of the formula (IV) as defined in any of claims 12-15 or 16-18 with one or more compounds of the formula (V) R'R"NH, where R' and R" are as defined in claim 12, 15, 17 or 18.

22. The process as claimed in claim 21, characterized in that the polymerization is carried out as a polycondensation at a temperature of $\leq 200°$ C.

23. The process as claimed in claim 22, characterized in that the polymerization is carried out under a reduced pressure of <90 kPa.

24. A polyborosilazane compound obtained by a process as claimed in claim 21, characterized in that the polyborosilazane compound is melted at a temperature in the range from 50 to 300° C., preferably from 100 to 150° C., and the melt reaches a viscosity of from 40 to 200 P·s, preferably from 90 to 120 P·s, and a loss factor of from 10 to 500, preferably from 50 to 100, within this temperature range.

25. A process for producing a silicon carboboronitride ceramic comprising tempering an oligoborosilazane or polyborosilazane as claimed in claim 20 at temperatures in the range from 800° C. to 1700° C. in an inert atmosphere or an amine- or $NH_3$-containing atmosphere.

26. A silicon carboboronitride ceramic obtained by a process as claimed in claim 25, characterized in that C—Si—N—B, Si—N—B—C or C—Si—N—B—C structural units are present in the ceramic and the elements Si,N,B and C are present in an amount of more than 93% by mass.

27. A silicon carboboronitride ceramic obtainable obtained by a process as claimed in claim 25, characterized in tat Si—N—B structural units are present in the ceramic and the elements Si,N,B and C are present in an amount of more than 93% by mass, in particular more than 97% by mass, with the proviso that $C \geq 3\%$ by mass.

28. A silicon carboboronitride ceramic as claimed in claim 26, characterized in that it is an amorphous silicon carboboronitride ceramic powder.

29. A process for producing a composite ceramic comprising SiC,$Si_3N_4$ and BN, comprising ageing a silicon carboboronitride ceramic as claimed in claim 26 at temperatures of >1700° C.

30. The process as claimed in claim 29, characterized in that an at least part crystalline composite ceramic is produced.

31. A composite ceramic obtained by a process as claimed in claim 29 by crystallization of a silicon carboboronitride ceramic as claimed in claim 29, characterized in that SiC, $Si_3N_4$ and BN are present in molecularly dispersed form.

32. Shaped ceramic bodies, ceramic fibers, ceramic coatings, or ceramic microstructures derived from the oligoborosilazane or polyborosilazane compounds of claim 20.

33. A process for producing ceramic materials as claimed in claim 26 comprising producing therewith shaped ceramic bodies, ceramic fibers, ceramic coatings or ceramic microstructures.

34. A ceramic fiber obtained by melt spinning an oligoborosilazane or polyborosilazane compound according to claim 20 in the monofilament or multifilament mode under an inert atmosphere, the spun green fiber is made infusible in situ in the spinning shaft and/or in a subsequent process step by treatment with a reactive gas selected from among $NH_3$, ethylenediamine, trichiorosilane, dichlorosilane, boranedimethyl sulfide adduct, borane-triethylamine adduct, $B_2H_6$ or by means of electromagnetic radiation or particle radiation and the cured green fiber is ceramicized at temperatures in the range from 800 to 1600° C., preferably 1200° C.

35. The melt spinning operation according to claim 34, characterized in that the melt temperature is from 50 to 300° C., preferably from 100 to 150° C., the capillary diameter of the spinneret is from 50 to 500 μm, preferably 300 μm, at a capillary length of from 1 to 30 mm, preferably from 5 to 10 mm, and the take-off velocity is from 150 to 1000 m/min, preferably from 300 to 600 mn/min.

36. A ceramic fiber as claimed in claim 34, characterized in that the fiber has a tensile strength of from 0.5 to 2 Gpa, preferably 1.5 Gpa, a modulus of elasticity of from 50 to 200 Gpa, preferably 150 Gpa, and an oxygen content of ≦3% by weight, preferably ≦1% by weight.

37. The ceramic microstructures as claimed in claim 32, characterized in that microstructures are produced by injection molding or lithographic processes.

38. A woven or braided fabric manufactured using the ceramic fibers of claim 32.

39. A process for making a ceramic coating using a borosilazane compound according to one of claims 12-15 comprising subjecting the compound to chemical vapor deposition (CVD) or physical vapor deposition (PVD).

40. A process for producing a silicon carboboronitride ceramic comprising tempering an oligoborosilazane or polyborosilazane as claimed in claim 24 at temperatures in the range from 800° C. to 1700° C. in an inert atmosphere or an amine- or $NH_3$-containing atmosphere.

41. A silicon carboboronitride ceramic as claimed in claim 27, characterized in that it is an amomhous silicon carboboronitride ceramic powder.

42. A process for producing a composite ceramic comprising $SiC,Si_3N_4$ and BN, comprising ageing a silicon carboboronitride ceramic as claimed in claim 27 at temperatures of >1700° C.

43. A composite ceramic obtained by a process as claimed in claim 42 by crystallization of a silicon carboboronitride ceramic as claimed in claim 42, characterized in that SiC, $Si_3N_4$ and BN are present in molecularly dispersed form.

44. Shaped ceramic bodies, ceramic fibers, ceramic coatings, or ceramic microstructures derived from the oligoborosilazane or polyborosilazane compounds of claim 27.

45. A process for producing a silicon carboboronitride ceramic, comprising tempering an oligoborosilazane or polyborosilazane compound as claimed in claim 20 at temperatures in the range from 800° C. to 1700° C. in an inert atmosphere or an amine- or $NH_3$-containing atmosphere.

46. A process for producing a silicon carboboronitride ceramic, comprising tempering an oligoborosilazane or polyborosilazane compound as claimed in claim 24 at temperatures in the range from 800° C. to 1700° C. in an inert atmosphere or an amine- or $NH_3$-containing atmosphere.

* * * * *

UNITED STATES PATENT AND TRADEMARK OFFICE
CERTIFICATE OF CORRECTION

PATENT NO.         : 7,297,649 B2  
APPLICATION NO. : 10/380605  
DATED                  : November 20, 2007  
INVENTOR(S)        : Martin Jansen et al.

Page 1 of 1

It is certified that error appears in the above-identified patent and that said Letters Patent is hereby corrected as shown below:

At column 18, line 42, delete "hal" and insert --Hal--.

At column 19, line 11, delete "alkyt" and insert --alkyl--.

At column 19, line 58, delete "obtainable".

At column 19, line 65, delete "er/and-".

At column 20, line 8, delete "$\leqq$" and insert --$\leq$--.

At column 20, line 16, delete "P·s" and insert --Pa·s--.

At column 20, line 17, delete "P·s" and insert --Pa·s--.

At column 20, line 29, delete "obtainable".

At column 20, line 31, delete "tat" and insert --that--.

At column 20, line 34, delete "$\geqq$" and insert --$\geq$--.

Signed and Sealed this

Eleventh Day of March, 2008

JON W. DUDAS  
*Director of the United States Patent and Trademark Office*

UNITED STATES PATENT AND TRADEMARK OFFICE
CERTIFICATE OF CORRECTION

PATENT NO. : 7,297,649 B2  Page 1 of 1
APPLICATION NO. : 10/380605
DATED : November 20, 2007
INVENTOR(S) : Martin Jansen et al.

It is certified that error appears in the above-identified patent and that said Letters Patent is hereby corrected as shown below:

On the title page, "(73) Assignee:", please add the following:

--Fraunhofer Gesellschaft zur Forderung der angewandten Forschung e.V., Munich (DE)--

Signed and Sealed this

Twenty-fifth Day of November, 2008

JON W. DUDAS
*Director of the United States Patent and Trademark Office*